United States Patent [19]

McPherson et al.

[11] Patent Number: 4,874,600

[45] Date of Patent: Oct. 17, 1989

[54] NO-CARRIER-ADDED [1[11]C]PUTRESCINE

[75] Inventors: Daniel W. McPherson, Baltimore, Md.; Joanna S. Fowler, Bellport; Alfred P. Wolf, Setauket, both of N.Y.

[73] Assignee: The United States of America as Represented by the United States Department of Energy, Washington, D.C.

[21] Appl. No.: 853,105

[22] Filed: Apr. 17, 1986

[51] Int. Cl.[4] .................. A61K 49/02; C07C 87/14
[52] U.S. Cl. ................................ 424/1.1; 424/9; 564/511
[58] Field of Search .................... 424/1.1, 9; 564/511

[56] References Cited

U.S. PATENT DOCUMENTS 2,647,146  7/1983  Arthur .
3,316,185  4/1967  Rewkin .
4,406,875  9/1983  de Jong et al. .................... 424/1.1

OTHER PUBLICATIONS

Jerabek et al., "Synthesis and Uptake of No-Carrier-Added 1-"C-Putrescine", Int. J. Nucl. Med. Biol., 1985, 12(5), pp. 349-352.
Merck's Organic Name Reactions, 10, 60.
Welch et al. "Carbon-11-Labeled Methylated Polyamine Analogs", J. Nucl. Med., 18, 1973, pp. 74-78.
Russell et al., "Polyamines as Biochemical Markers", Prog. Can. Res. Ther., 8, 1978, pp. 1-4, 6, 127-138, 144-149.
Winstead et al., "Relationship of Molecular Structure to In viro Distribution", Env. J. Nuclo. Med., 5, pp. 165-169, (1980).
Volkow et al., "Labeled Putrescine as a Probe in Brain Tumors", Science, 221, p. 673, (1983).
Beaney, "PET in Study of Human Tumors", Serv. in Nucl. Med., XIV, 4, 324-340, (1984).
McPherson et al., Syn. and Biodistribution, of No-Carrier-Added [1-$^{11}$C] Putrescine., J. Nucl. Med., 26, Oct. 1985, 1186-1189.

*Primary Examiner*—John S. Maples
*Attorney, Agent, or Firm*—Margaret C. Bogosian; Paul A. Gottlieb; Judson R. Hightower

[57] ABSTRACT

The invention relates to a new radiolabeled imaging agent, no-carrier-added [1-$^{11}$C]putrescine, and to the use of this very pure material as a radiotracer with positron emission tomography for imaging brain tumors. The invention further relates to the synthesis of no-carrier-added [1-$^{11}$C]putrescine based on the Michael addition of potassium $^{11}$C-labeled cyanide to acrylonitrile followed by reduction of the $^{11}$C-labeled dinitrile. The new method is rapid and efficient and provides radiotracer with a specific activity greater than 1.4 curies per millimol and in a purity greater than 95%.

3 Claims, No Drawings

NO-CARRIER-ADDED [1-11C]PUTRESCINE

The U.S. Government has rights in this invention pursuant to Contract Number DE-AC02-76CH00016, between the U.S. Department of Energy and Associated Universities Inc.

BACKGROUND OF THE INVENTION

The application of positron emission tomography (PET) to the study of human tumors and to the study of the response of such tumors to different therapeutic approaches continues to be of interest. Of particular interest are studies where valid tracer kinetic models exist and physiological quantitation is possible. Such kinetic models are the result of a thorough understanding of the biochemistry of the tracer in the tumor and in the surrounding tissue.

Polyamines have been investigated for use as biochemical markers for malignancy, including brain tumors. Since adult brain parenchyma does not normally divide, a polyamine that marks cell growth and proliferation should be taken up and metabolized solely by the brain tumor. Volkow, et al. [*Science*, 221, 673 (1983)] tested the feasibility of using the polyamine putrescine, labeled with [$^3$H] and [$^{14}$C], as a PET tracer for brain tumors. They found that in vivo uptake into transplanted rat glioma was 35 times greater than in normal brain tissue and that metabolism to spermine by the tumor was rapid, in contrast to adjacent normal brain tissue. Winstead, et al. [*Eur. J. Nucl Med.*, 5, 165 (1980)] synthesized carbon-11 labeled putrescine, but the synthesis yielded only carrier contaminated material that had too low a specific activity to be acceptable for human studies.

Studies such as the Volkow, et al. study showed the usefulness of the putrescine model but also showed that because of impurities, very low specific activity, inappropriate half-lives, or non-optimum radiation emission, the carrier-added-[$^{11}$C], the [$^3$H] and the [$^{14}$C] radiolabels were not suitable for the preparation of a tracer for human studies of brain tumors using PET.

One purpose of the present invention is to overcome these deficiencies of the prior art by providing a no-carrier-added [$^{11}$C]-labeled putrescine material that is a useful tracer when used with PET for quantitating the degree of malignancy in vivo and for monitoring response to radio- and chemotherapy.

Another purpose of the present invention is to provide a synthesis of the no-carrier-added [1-$^{11}$C]putrescine in sufficiently high purity and specific activity to avoid significantly perturbing the plasma concentration of the endogenous diamine.

SUMMARY OF THE INVENTION

The instant invention lies in the field of radiotracers used with positron emission tomography (PET). More specifically, the instant invention covers the new radiotracer, no-carrier-added [1-$^{11}$C]putrescine, the method of preparing this material, and the method of using this material with positron emission tomography as a selective metabolic tracer for imaging brain tumors.

No-carrier-added [1-$^{11}$C]putrescine provides the appropriate tracer kinetic model for quantifying tumor growth rate in human brains and for monitoring response to radiotherapy and chemotherapy using positron emission tomography. The application of this PET method for imaging and detecting the tumor growth rate requires that the putrescine radiolabeled with carbon-11 at the 1-C position be prepared in a sufficiently high radiochemical purity and specific activity to adapt it for imaging brain tumors in humans. The present invention provides a new synthesis of no-carrier-added [1-$^{11}$C]putrescine; the resulting material has a specific activity greater than 1.4 curies/μmol (EOB) and is produced at a purity of at least 95%, usually from 97% to 98%, radiochemical purity, as assayed by thin layer chromatography. The minor impurity present, in an amount of less than 3%, is $^{11}$C-labeled 3-aminobutyronitrile.

DETAILED DESCRIPTION OF THE INVENTION

This invention provides the new brain imaging agent no-carrier-added [1-$^{11}$C]putrescine through a highly efficient novel synthesis. The no-carrier-added [1-$^{11}$C]putrescine is prepared by the Michael addition of a no-carrier-added alkali metal [$^{11}$C]cyanide, preferably no-carrier-added [$^{11}$C]potassium cyanide, to acrylonitrile followed by the subsequent reduction of the $^{11}$C-labeled dinitrile. This reduction is carried out by a suitable mild reducing agent such as boranemethylsulfide complex. The no-carrier-added [1-$^{11}$C]putrescine produced in this manner is of a suitable purity (95–99%) and specific activity (greater than 1.4 curies per micromole) to adapt it for use in humans in PET studies of cerebral malignancy. Using an appropriate and radiologically tolerable dose for PET studies of cerebral malignancy, no-carrier-added [1-$^{11}$C]putrescine having a purity of at least 95% and a specific activity of greater than 1.4 curies/μmol is injected into the patient. After administration of the tracer, the PET image is taken of the brain area. Accumulation of the tracer in the tumor will provide an accurate measure of the malignancy in the brain because of the low uptake of the tracer in normal brain tissue. Tissue distribution studies in normal mice showed the expected low uptake of the tracer in the normal brain. The no-carrier-added [1-$^{11}$C]putrescine of the present invention is of a suitable purity and specific activity for use in humans in PET studies of cerebral malignancy.

No-carrier-added [1-$^{11}$C]putrescine is prepared according to the following reaction sequence:

$$CH_2=CHCN + K[^{11}C]N \longrightarrow$$

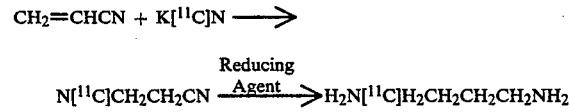

$$N[^{11}C]CH_2CH_2CN \xrightarrow{\text{Reducing Agent}} H_2N[^{11}C]H_2CH_2CH_2CH_2NH_2$$

No-carrier-added [1-$^{11}$C]putrescine is synthesized in a synthesis time of about 50 minutes by the above Michael addition. Potassium[$^{11}$C]cyanide is added to acrylonitrile in a suitable oxygenated inert solvent, such as a furan, preferably tetrahydrofuran, followed by reduction of the $^{11}$C-labeled dinitrile with a suitable reducing agent such as borane or boranemethylsulfide complex, with boranemethylsulfide complex being preferred.

EXAMPLE 1

Preparation of No-carrier-added [1-$^{11}$C]putrescine Materials

The acrylonitrile used is of commercial grade and is distilled prior to use. The anhydrous methanol-hydrogen chloride is prepared by drying the methanol with CaSO$_4$, distilling it into a flask and bubbling HCl gas, dried by passing through concentrated sulfuric acid, into the methanol until the solution is 4–6N by weight. Tetrahydrofuran is dried over sodium/benzophenone and distilled prior to use. Other related furans may be used as examples of oxygenated inert solvents for the reaction medium.

Radiochemical Assay

Radiochemical and chemical purity is assayed by thin layer chromatography (TLC) on Silica Gel G by spotting [1-$^{11}$C]putrescine with authentic carrier material and showing that the radioactivity was coincident with the spot corresponding to the authentic compound. In the TLC system of acetone:water:propionic acid (6:4:2) saturated with sodium chloride, putrescine has an R$_f$ value of 0.33 visualized with ninhydrin. The radiochemical purity is also assayed by high performance liquid chromatography (HPLC) as putrescine and also as the dibenzoyl derivative of putrescine [Redmond, et al., J. Chromat., 170, 479 (1979)]. For putrescine, a Bio-Rad Aminex HPX-72-0 column (300 mm×7.8 mm) is used with 0.03M sodium hydroxide as the mobile phase. Putrescine is detected at 220 nm. For the dibenzoyl derivative of putrescine, a reverse phase C$_8$ column is used with a methanol-water (52:48) mobile phase. In both cases, authentic carrier is added. The elution profile of the radioactivity is congruent with the carrier. Specific activity is determined to be greater than 1.4 Ci/μmol by gas chromatographic analysis (4:1 DMS-KOH s.s. 6 ft×⅛ in, thermal conductivity detector). The analyses are performed using a calibration curve a peak area versus nmol concentration of seven standard putrescine solutions of 98.6 to 12.3 nm. The retention time of the authentic putrescine standards is 6.0 minutes with a helium flow rate of 50 ml/min.

Carbon-11-labeled hydrogen cyanide is produced according to Christman, et al. [Int. J. Appl. Radiat. Isot., 26, 435 (1975)], and trapped in 0.2 ml of a 0.1% potassium hydroxide solution. Acrylonitrile (0.5 ml) and tetrahydrofuran (0.5 ml) are added and the solution stirred and heated at 65° C. for 5 min. The solution is evaporated to dryness under vacuum; ethanol (2×0.25 ml) is added and removed in vacuo to remove the residual acrylonitrile and water. The residue is taken up in 1.0 ml of dry tetrahydrofuran and passed through a drying tube containing anhydrous potassium carbonate and potassium hydroxide pellets into a flask fitted with a reflux vessel. A slow stream of nitrogen is bubbled through the mixture and 1.5 ml of a 2M boranemethyl-sulfide complex solution in tetrahydrofuran is added. The solution is stirred and refluxed at 140° C. for 10 min. The solution is then cooled and 0.5 ml of an anhydrous methanol-hydrochloric acid solution is slowly added. The mixture is evaporated to dryness under vacuum. A small amount of white residue is present and this is taken up in 1.0 ml of a 0.03M sodium hydroxide solution and transferred to a syringe fitted with a 0.45μ filter.

The reaction vessel is then rinsed with 0.5 ml of the 0.03M sodium hydroxide solution and this is also transferred to the syringe. The reaction mixture is filtered and the filter washed with 0.5 ml of the sodium hydroxide solution. The filtrate is injected onto a Bio-Rad Aminex HPX-72-0 HPLC column (300 mm×7.8 mm) using a 0.03M sodium hydroxide solution as the mobile phase. No-carrier-added [1-$^{11}$C]putrescine has a retention time of about 10 minutes with a flow rate of 1.5 ml/min. The diamine is collected over a period of 2.0 min. and is contained in a volume of 3.0 ml. The diamine is made isotonic by the addition of sterile solutions of 1M hydrogen chloride (0.70 ml) and 1M sodium bicarbonate (0.65 ml). This solution is filtered (sterile 0.22 μM millipore) into a sterile injection vial. The filter is washed with 0.5 ml of a sterile saline solution which is also collected in the injection vial. The reaction time is about 50 minutes and the radiochemical yield is 20% at end of bombardment (EOB) based on the starting activity of hydrogen [$^{11}$C]cyanide produced at the end of cyclotron bombardment. In a typical experiment using a ten-minute cyclotron beam, 207 μCi of hydrogen [$^{11}$C]cyanide is produced and 7.5 μCi of no-carrier-added [1-$^{11}$C]putrescine is obtained after a synthesis time of 50 minutes. Radiochemical purity is assayed by thin-layer chromatography and found to have greater than 97.0% purity with $^{11}$C-labeled 3-aminobutyronitrile as the minor impurity.

Table 1 below shows the conditions of temperature and time for maximum yield of no-carrier-added [1-$^{11}$C]putrescine.

TABLE 1

| Yield of the [$^{11}$C]Dinitrile from the Reaction of Acrylonitrile and Potassium [$^{11}$C]Cyanide | | | | |
|---|---|---|---|---|
| Temp. (°C.) | Time (min) | Acrylonitrile (ml) | Tetra-hydrofuran (ml) | 1% KOH Solution (ml) | % Yield[a] |
| 65 | 5 | 0.50 | 0.50 | 0.20 | 73.9 |
| 65 | 5 | 0.10 | 0.20 | 0.10 | 57.0 |
| 65 | 5 | 0.02 | 0.20 | 0.04 | 38.6 |
| 65 | 5 | 0.02 | 0.20 | 0.10 | 23.7 |
| 65 | 5 | 0.03 | 0.30 | 0.015 | 40.3 |
| 65 | 5 | 0.05 | 0.30 | 0.025 | 48.8 |
| 48 | 10 | 1.40 | 0.50 | 0.20 | 62.8 |
| 48 | 5 | 1.40 | 0.50 | 0.20 | 64.6 |
| 48 | 10 | 0.50 | 0.50 | 0.20 | 88.2 |
| 48 | 5 | 0.50 | 0.50 | 0.20 | 44.0 |
| 48 | 10 | 0.20 | 0.20 | 0.20 | 34.1 |
| 48 | 10 | 0.20 | 0.40 | 0.20 | 41.6 |

[a]Yield from EOB from hydrogen [$^{11}$C]cyanide produced. Analyzed by gas chromatography and compared to carrier succinonitrile.

EXAMPLE 2

Tissue Distribution Studies in Mice

Male Swiss albino mice (BNL strain, 20–32 g) were used in this study. No-carrier-added [1-$^{11}$C]putrescine (0.05–0.20 μCi/mouse of specific activity greater than 1.4 Ci/μmol; 36–140 pmol/mouse) was injected by tail vein into mice and the animals were killed by cervical dislocation at the desired time interval (5, 30 and 60 minutes). The various organs were rapidly removed, blotted free of blood and placed in preweighed counting vials and the vials were sealed. Tissue samples as well as injection standards were counted in a Packard automated sodium iodide well counter. Both percent injected dose per gram of tissue and percent injected dose per organ were determined from the decay corrected activity.

Table 2 below shows the results of the biodistribution of the no-carrier-added [1-$^{11}$C]putrescine in the mice.

TABLE 2

| Tissue Distribution (% Dose/Organ)[a] of no-carrier-added [1-$^{11}$C]putrescine in Mice at 5, 30 and 60 Minutes[b] | | | |
|---|---|---|---|
| | Sacrifice Time (Min) | | |
| Organ | 5 Min | 30 Min | 60 Min |
| Blood[c] | 1.37 ± 0.18 | 0.82 ± 0.11 | 0.76 ± 0.46 |
| Brain | 0.12 ± 0.01 | 0.15 ± 0.01 | 0.13 ± 0.01 |

TABLE 2-continued

Tissue Distribution (% Dose/Organ)[a] of no-carrier-added [1-$^{11}$C]putrescine in Mice at 5, 30 and 60 Minutes[b]

| Organ | Sacrifice Time (Min) | | |
|---|---|---|---|
| | 5 Min | 30 Min | 60 Min |
| Heart | 0.19 ± 0.04 | 0.15 ± 0.02 | 0.12 ± 0.01 |
| Lungs | 0.57 ± 0.08 | 0.48 ± 0.08 | 0.43 ± 0.08 |
| Liver | 5.96 ± 1.2 | 4.85 ± 0.75 | 3.70 ± 0.50 |
| Spleen | 0.57 ± 0.35 | 0.56 ± 0.25 | 0.48 ± 0.16 |
| Kidney | 10.5 ± 2.0 | 2.63 ± 0.36 | 1.27 ± 0.21 |
| Small Intestine | 13.7 ± 5.0 | 7.61 ± 2.00 | 4.40 ± 1.66 |

[a]Each value represents the average ± S.D. of 6 mice.
[b]n = 6 mice/time
[c]% dose/g Note that in Table 2 above, the uptake in normal brain at 5, 30 and 60 minute periods is very low, a requirement for a high signal:noise ratio for imaging human brain tumors permitting a physician to read the image and select in a quantitative manner the course of the tumor development by repeating the procedure. Only with the present no-carrier-added [1-$^{11}$C]putrescine based on the Michael addition and reduction has a specific activity of greater than 1.4 curies/micromole been obtained to provide the essential tracer activity for the method to work efficiently.

Table 2 shows the accumulation of activity is less in the normal brain than for other tissues. Most of the no-carrier-added [1-$^{11}$C]putrescine was taken up by the liver, kidneys, and small intestine. As expected, the diamine is not accumulating in the normal brain tissue and therefore will be an effective tracer for quantitating malignancies in the brain because the accumulation of activity in the tumor will be readily imaged by PET.

We claim:

1. A method of imaging brain tumors which comprises injecting a radiologically tolerable dose of no-carrier-added [1-$^{11}$C]putrescine having a radiochemical purity of at least 95% and a specific activity greater than 1.4 curies per micromole and then taking an image of the brain area with positron emission tomography.

2. A method of monitoring the effectiveness of chemotherapy and/or radiotherapy of brain tumors which comprises:
   (1) prior to the commencement of said therapy, injecting a radiologically tolerable dose of no-carrier-added [1-$^{11}$C]putrescine having a radiochemical purity of at least 95% and a specific activity of greater than 1.4 curies/micromole and then taking an image of the brain area with positron emission tomography; and
   (2) at selected intervals during said therapy, repeating the imaging process using said no-carrier-added [1-$^{11}$C]putrescine with positron emission tomography to monitor response to said therapy.

3. No-carrier-added [1-$^{11}$C]putrescine having a radiochemical purity of greater than 95% and having a specific activity greater than 1.4 curies per micromole.

* * * * *